United States Patent [19]

Huang

[11] Patent Number: 4,618,603

[45] Date of Patent: Oct. 21, 1986

[54] ALPHA-HETEROCYCLIC CARBINOL PHOSPHATES

[75] Inventor: Jamin Huang, Chapel Hill, N.C.

[73] Assignee: Union Carbide Corporation, Danbury, Conn.

[21] Appl. No.: 779,634

[22] Filed: Sep. 24, 1985

Related U.S. Application Data

[63] Continuation of Ser. No. 364,073, Mar. 31, 1982, abandoned.

[51] Int. Cl.$^4$ .............. A01N 57/16; A01N 57/32; C07D 263/56; C07D 263/14
[52] U.S. Cl. ............................. 514/80; 548/113
[58] Field of Search ..................... 548/113; 514/80

[56] References Cited

U.S. PATENT DOCUMENTS

| | | | |
|---|---|---|---|
| 2,877,155 | 3/1959 | Metivier | 548/113 X |
| 3,674,803 | 7/1972 | Scherer et al. | 548/113 |
| 3,890,336 | 6/1975 | Suzuki et al. | 548/119 |
| 4,062,951 | 12/1977 | Sauli | 548/113 X |
| 4,137,308 | 1/1979 | Gutman | 514/92 |
| 4,212,861 | 7/1980 | Theobald et al. | 548/119 X |
| 4,425,338 | 1/1984 | Huang | 548/113 X |

FOREIGN PATENT DOCUMENTS

| | | |
|---|---|---|
| 647745 | 5/1964 | Belgium . |
| 1137257 | 9/1962 | Fed. Rep. of Germany . |
| 1161275 | 1/1964 | Fed. Rep. of Germany . |
| 1267466 | 12/1968 | Fed. Rep. of Germany . |
| 1162422 | 9/1958 | France . |
| 2168184 | 8/1973 | France . |
| 2193022 | 2/1974 | France . |
| 49-00442 | 1/1974 | Japan . |
| 49-11623 | 6/1974 | Japan . |
| 52-76436 | 6/1977 | Japan . |
| 6607822 | 12/1966 | Netherlands . |
| 766383 | 10/1976 | South Africa . |
| 932388 | 7/1963 | United Kingdom . |
| 965520 | 7/1964 | United Kingdom . |

OTHER PUBLICATIONS

Pianka et al., Chem. Abst., 69: 77365C, 66436C, (1968).

*Primary Examiner*—Richard L. Raymond
*Attorney, Agent, or Firm*—Gerald L. Coon

[57] ABSTRACT

Novel alpha-heterocyclic carbinol phosphates have been found to exhibit insecticidal and miticidal activity.

21 Claims, No Drawings

ALPHA-HETEROCYCLIC CARBINOL PHOSPHATES

This application is a continuation of prior U.S. application: Ser. No. 364,073, filing date Mar. 31, 1982, now abandoned.

This invention relates to a novel insecticidal and miticidal alpha-heterocyclic carbinol phosphates. This invention also relates to pesticidal compositions for controlling insects and mites, as well as to methods of controlling insects and mites by subjecting them to an insecticidally or miticidally effective amount of the compounds of this invention.

The novel compounds of this invention are compounds of the formula:

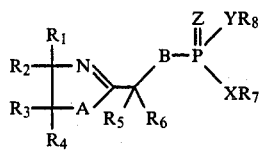

wherein:

A is O, S or $NR_9$;
$R_9$ is hydrogen or $C_1$ or $C_6$ alkyl;
B is O, S or NH;
X is O or S;
Y is O, S or NH;
Z is O or S;
$R_7$ and $R_9$ are individually $C_1$ to $C_6$ alkyl;
$R_1$, $R_2$, $R_3$ and $R_4$ are individually hydrogen, alkyl, haloalkyl, alkenyl, alkynyl, cycloalkyl, cycloalkenyl, aryl, aryl substituted with one or more nitro, halogen alkyl, trifluoroalkyl, cyano, alkoxy, and alkylthio groups;
$R_1$ and $R_3$, $R_2$ and $R_4$ are together or independently a cyclic ring of 3–6 atoms; or
$R_1$ and $R_2$, $R_3$ and $R_4$ are together or independently a cyclic ring of 4–6 atoms; or
$R_1$, $R_2$, $R_3$ and $R_4$ together form a 6-membered aromatic ring which is non-substituted or alkyl, halo, alkoxy, alkylthio, alkylamino or dialkylamino substituted alkyl; alkoxy, alkylthio, halo, nitro, cyano, trifluoromethyl, phenoxy, phenylthio, alkoxycarbonyl, trifluoromethoxy, alkylaminocarbonyl, dialkylaminocarbonyl, alkanoyl, aroyl, alkenyl or alkynyl substituted; or
$R_2$ and $R_4$ is a chemical bond and $R_1$ and $R_3$ is alkoxy, alkylthio, nitro, halogen, cyano, phenoxy or phenylthio;
$R_5$ and $R_6$ are individually hydrogen, cyano, alkyl, alkenyl, haloalkenyl, cycloalkenyl, or alkynyl;
non-substituted pyridyl, 2-benzothiazole, 2-benzoxazole, furanyl or thiophenyl; or halo, nitro, cyano, trifluoromethyl, alkyl, alkoxy, alkoxycarbonyl, alkylaminocarbonyl, dialkylaminocarbonyl, alkanoyl or aroyl substituted pyridyl, 2-benzothiazole, 2-benzoxazole, furanyl, or thiophenyl; or
together form a cyclic ring of 4–6 atoms
with the proviso that
(a) when $R_5$ and $R_6$ are either hydrogen or lower alkyl, $X \neq Y$ and
(b) when $R_5$ and $R_6$ are both hydrogen, B is sulfur and Y is —NH—, then X cannot be oxygen.

Generally, the preferred compounds of this invention are those wherein:

A is O or S;
B is O or S;
X is O;
Y is S;
$R_1$, $R_2$, $R_3$ and $R_4$ together form a 6-membered aromatic ring which is non-substituted or alkyl or halo, alkoxy, alkylthio, alkylamino or dialkylamino substituted alkyl; alkoxy, alkylthio, halo, nitro, cyano, trifluoromethoxy, trifluoromethyl, phenoxy, phenylthio, alkoxycarbonyl, alkylaminocarbonyl, dialkylaminocarbonyl, alkanoyl, aroyl, alkenyl or alkynyl substituted; and $R_5$ is hydrogen.

Generally, the more preferred of the preferred compounds of this invention are those wherein:

$R_7$ is ethyl
$R_8$ is n-propyl
$R_6$ is hydrogen or $C_1$ to $C_6$ alkyl.

The most preferred compounds of this invention are the following:

S-[1-(2-benzoxazolyl)-ethyl]-O-ethyl-S-n-propyl dithiophosphate
O-[1-(2-benzothiazolyl)-methyl]-O-ethyl-S-n-propyl thiophosphate
O-[1-(2-benzothiazolyl)-ethyl]-O-ethyl-S-n-propyl thiophosphate.

The novel alpha-heterocyclic carbinol phosphates of this invention can be conveniently prepared by the general reaction methods or modifications thereof set forth below. The preparation can consist of two steps: step one consists of the preparation of appropriate alcohols, thiols and amines; step two consists of a phosphorylation reaction.

In the following methods,
A, $R_1$, $R_2$, $R_3$, $R_4$, $R_5$ and $R_6$ are as described previously; B is 0 or 5;
$X^1$ is $OCH_3$, $OCH_2CH_3$, Cl, or

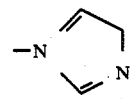

$Y^1$ is Li, Na⊕, or MgBr⊕
Q may be Cl, Br $OSO_2CH_3$,

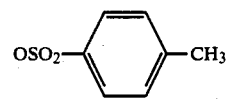

M⊕ may be alkali metal, alkline earth metal or ammonium cation or a cation of an organic base.

Step one, the preparation of appropriate alcohols and/or thiols, can be achieved by the following methods.

METHOD I

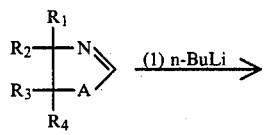

METHOD I

-continued

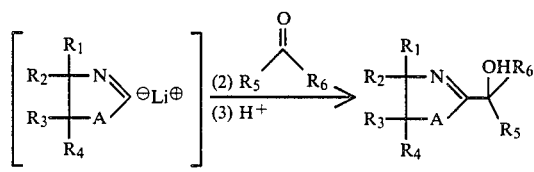

The substituted 2-(4,5-dihydro-1,3-azole)methanols and 2-(1,3-azole)methanols illustrated in METHOD I can be effected by metallation of 4,5-dihydro-1,3-azoles and 1,3-azoles with one equivalent of n-butyllithium at −78° C., followed by the addition of appropriate aldehydes or ketones. This reaction may be performed in anhydrous diethyl ether or tetrahydrofuran.

METHOD II

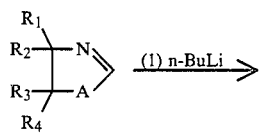

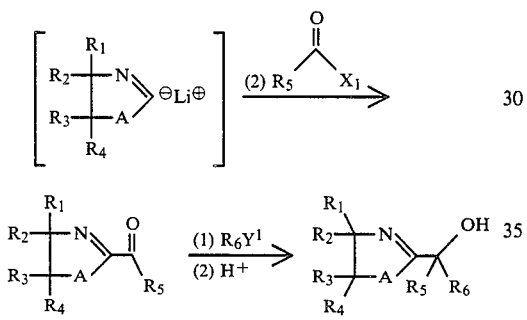

The preparation of ketones or aldehydes in Method II can be achieved by metallation of 4,5-dihydro-1,3-azoles and 1,3-azoles as described in Method I, followed by the addition of appropriate methyl esters (or ethyl esters, acid chlorides, acyl imidazoles, alkyl nitrile). The desired carbinols can then be effected by nucleophilic addition of appropriate organometallic compounds (such as alkyllithium, Grignard reagents) or nitrile on toward the ketones or aldehydes.

METHOD III

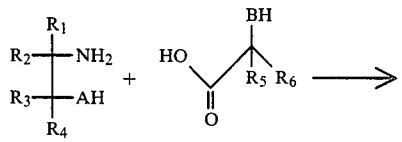

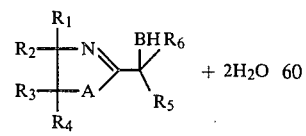

The condensation reaction outlined in Method III can be accomplished using essentially equimolar ratios of the alpha-hydroxy acids (or alpha-thio acids) and appropriate 2-aminoethanols (or 2-aminoethanethiols, 1,2-diaminoethanes, O-aminophenols, O-aminothiophenols, O-aminoanilines) in a variety of conditions. This may be effected by azeotropically removing water via an inert, high-boiling organic solvent such as xylene. It can also be achieved by refluxing the two components in aqueous hydrochloric acid solution or heating the two reagents in a sealed tube at an elevated temperature.

METHOD IV

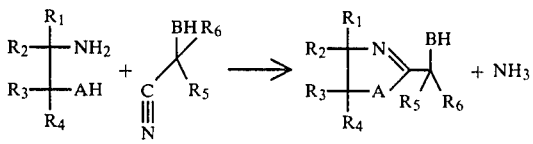

The reaction of Method IV can be conducted using equimolar ratios of the alpha-hydroxy nitrile (or alpha-thio nitrile) and appropriate 2-aminoethanols, (or 2-aminolthanethiols, 1,2-diaminoethanes, O-aminophenols, O-aminothiophenols, O-aminoanilines) in refluxing methanol.

METHOD V

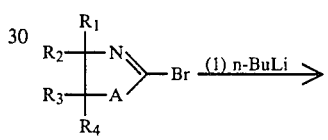

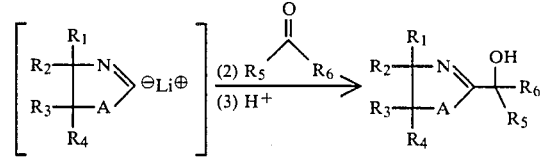

The reaction as outlined in Method V can be accomplished by halogen-lithium exchange of 2-bromo-1,3-azoles or 2-bromo-4,5-dihydro-1,3-azoles with one equivalent of n-butyllithium at −78° C. The corresponding lithium anion can then react with a variety of aldehydes or ketones to form desired alcohols. This reaction can be performed in anhydrous diethylether or tetrahydrofuran.

Preparation of appropriate amines can be achieved by the following reaction schemes.

METHOD VI

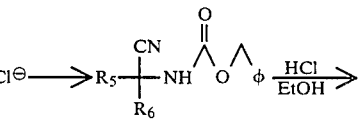

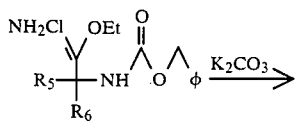

-continued
METHOD VI

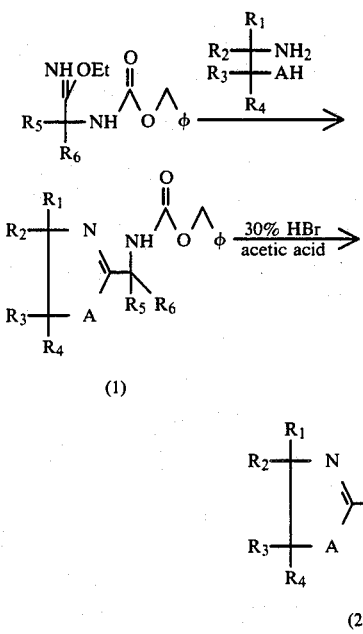

The reaction scheme illustrated in Method VI can be effected by protecting the alpha-amino nitrile with a benzyloxycarbonyl group. The nitrile is treated with dry hydrogen chloride in a mixture of absolute ethanol and absolute ether to yield the corresponding iminoether hydrochloride. Free iminoether can be obtained from the hydrochloride by removal of hydrogen chloride by treatment with aqueous concentrated potassium carbonate solution. Coupling of the iminoether with appropriate 2-aminoethanols (or 2-aminoethanethiols, 1,2-diaminoethanes, O-aminophenols, O-aminothiophenols, O-aminoanilines) gives protected amine (1) which can then be treated with 30% hydrogen bromide in acetic acid to afford the desired amine hydrobromide (2).

METHOD VII

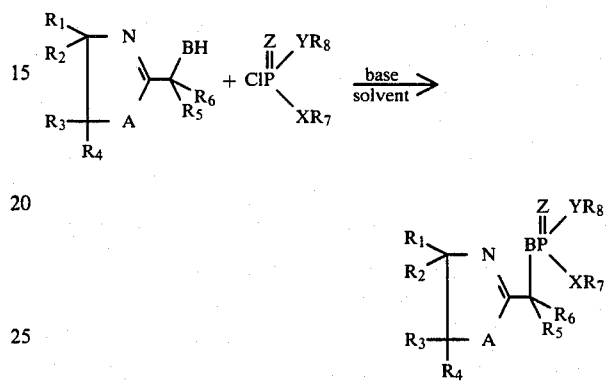

$R_{14}$ through $R_{17}$ are the substituents defined under the preferred compounds of this invention, i.e., when $R_1$ through $R_4$ form a six membered aromatic ring.

The reaction scheme outlined in Method VII demonstrates the preparation of amines. It can be achieved by the formation of the appropriate oxime, followed by reduction with powdered zinc in aqueous amomonia.

METHOD VIII

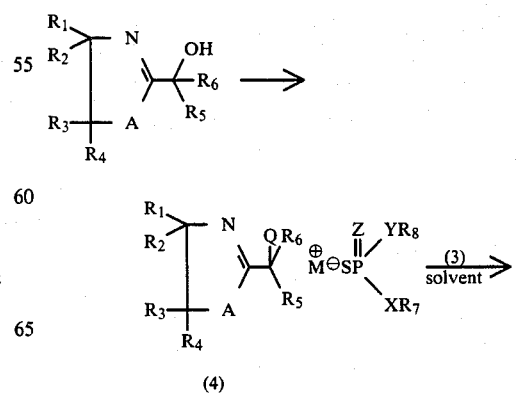

The phosphorylation illustrated in Method VIII can be achieved by reaction with appropriate phosphorylating agent in the presence of acid acceptor. Suitable acid acceptors are tertiary amine bases such as triethylamine or pyridine or preferably N,N'-dimethyl-4-aminopyridine. This reaction may be performed in a variety of organic solvents including methylene chloride, ethyl acetate, acetonitrile. This reaction can be conducted with temperatures ranging from 20° C. to 50° C. The resulting phosphates are viscous oils which are normally purified by Florisil chromatography (100–200 mesh) elutin with 5% ethyl acetate in hexane and increasing solvent polarity with ethyl acetate.

The preparation of these phosphates may also be achieved as shown in Method IX, by reacting salts of appropriate phosphoric acid of formula 3 with 4 in a variety of solvents. Illustrative of these organic solvents are methanol, ethanol and acetone.

METHOD IX

-continued
METHOD IX

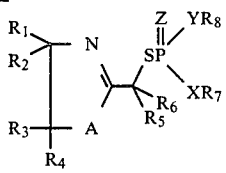

In general, the alcohols prepared in Methods I to V and the amines synthesized in Methods VI and VII are known compounds or can be prepared in accordance with conventional methods known to those skilled by the art.

The phosphorous halides and the salts of the phosphoric acid in Methods VIII and IX respectively generally are known materials in the art and can be obtained fom commercial sources or prepared in accordance with conventional methods known to those skilled in the art.

The following examples are illustrative of the methods of preparing the novel compounds of this invention.

EXAMPLE I 1-(2-benzoxazolyl)ethanethiol

A mixture of thiolactic acid (18.7 g.) and O-aminophenol (17.5 g.) was refluxed in xylene with a Dean-Stark tube overnight.

After cooling, the solution was washed with 1N HCl aqueous solution (2×500 ml.), 5% $NaHCO_3$ aqueous solution (2×500 ml.) and brine. It was dried over $Na_2SO_4$, filtered and concentrated in vacuo to yield desired product (8 g.). Anal. $C_9H_9NOS$: Calc: C, 60.30; H, 5.06; N, 7.82,
Found: C, 60.90; H, 5.09; N, 7.67.

EXAMPLE II

S-[1-(2-benzoxazolyl)-ethyl]-O-ethyl-S-n-propyl dithiophosphate

A mixture of O-ethyl-S-n-propyl phosphorochloridate (6.7 g.), and methylene chloride (15 ml.) was added to the solution of 1-(2-benzoxazolyl)ethanethiol (4.0 g.), N,N'-dimethyl-4-aminopyridine (2.93 g.), triethylamine (2.43 g.) and methyl chloride (100 ml.) at room temperature, and refluxed with drying tube for two days.

The solution was cooled to room temperature, and washed with water, dried over $Na_2SO_4$, filtered and concentrated in vacuo. The crude product was chromatographed on Florisil (100–200 mesh, 170 g.) utilizing a hexane-ethyl acetate increasing polarity gradient. The desired phosphate (1.5 g.) was afforded, nD 22 degrees: 1.6735.

Anal. $C_{14}H_{20}NO_3PS_2$: Calc: C, 48.68; H, 5.84; N, 4.06, Found: C, 47.56; H, 5.98; N, 4.26.

The following compounds are illustrative of this invention, all of which can be conveniently prepared by the processes of this invention simply by selecting appropriate starting materials.

| A | B | Z | X | Y | R₁ | R₂ | R₃ | R₄ | R₅ | R₆ | R₇ | R₈ |
|---|---|---|---|---|---|---|---|---|---|---|---|---|
| O | S | O | O | S | H | H | H | H | H | CH₃ | Et | n-Pr |
| S | O | O | O | S | Cl | — | H | — | H | CN | Et | n-Pr |
| S | O | S | O | S | Cl | H | H | H | H | CF₃ | Et | n-Butyl |
| O | S | O | O | S | Ph | H | H | H | H | —C≡C—CH₃ | Et | i-Pr |
| O | O | O | O | NH | —(CH₂)₄— | H | H | H | H | cyclohexyl | Et | Et |
| O | O | O | O | NH | NO₂ | — | H | — | CH₃ | CF₃ | Me | Et |
| S | O | S | S | S | CF₃ | — | H | — | H | cyclohexenyl | Et | n-Pr |
| O | O | O | O | NH | 2,6-Cl₂-C₆H₃ | H | H | H | —(CH₂)₅— | | n-Pr | n-Pr |
| S | O | S | O | S | H | H | —CH₂OCH₃ | H | H | —C(=O)OCH₃ | Et | Et |
| O | O | O | O | S | —CH₂SΦ | H | H | H | H | —C(=O)NHCH₃ | Et | n-Butyl |

Structural formula referenced by table:

$$R_1R_2C\text{—}A(R_3R_4)\text{—}C(R_5)(R_6)\text{—}N\text{=}BP(Z)\text{—}YR_8,\ XR_7$$

-continued

| A | B | Z | X | Y | (subst.) | R'2 | R'3 | | | R5 | R6 | R7 | R8 |
|---|---|---|---|---|---|---|---|---|---|---|---|---|---|
| O | O | S | O | S | —CH₂S—φ | — | H | — | — | H | CH₃C(=O)— | Et | n-Pr |
| O | S | O | O | S | i-Pr | H | H | — | — | H | CH₂=CH—CH₂— | Et | n-Pr |
| S | O | S | O | S | CH₃S— | — | H | — | — | H | (furyl) | Et | n-Pr |
| S | NH | NH | O | S | CF₃ | — | H | — | — | H | (pyridyl) | Et | n-Pr |
| O | O | S | O | S | CH₃ | CH₃ | H | H | — | CH₃ | CN | Et | n-Pr |
| O | O | S | O | S | H | H | H | H | — | H | H | Et | n-Pr |
| O | O | O | O | NH | (CH₃)₂NCH₂— | — | H | — | — | CH₃ | CH₃ | Et | Et |

Structure:

$$\text{R'}_1, \text{R'}_2, \text{R'}_3, \text{R'}_4\text{-benzo-}[N=C(\text{A})\text{-C}(R_5)(R_6)\text{-BP}(=Z)(\text{XR}_7)(\text{YR}_8)]$$

| A | B | Z | X | Y | R'₁ | R'₂ | R'₃ | R'₄ | R₄ | R₅ | R₆ | R₇ | R₈ |
|---|---|---|---|---|---|---|---|---|---|---|---|---|---|
| S | S | O | O | S | H | H | H | H | H | H | H | Et | n-Pr |
| O | O | O | O | S | H | H | H | H | H | CH₃ | H | Et | n-Pr |
| S | O | O | O | S | H | Cl | H | H | H | CF₃ | H | Et | n-Pr |
| O | O | O | O | S | H | NO₂ | H | H | Cl | CN | CH₃ | Et | Et |
| O | O | S | O | S | CF₃ | H | CF₃ | H | H | CN | H | Et | n-Pr |
| S | S | O | O | NH | H | CH₃ | H | H | Cl | (cyclohexyl-S—) | H | Me | i-Pr |

-continued

| | | | | | | | | | | | | |
|---|---|---|---|---|---|---|---|---|---|---|---|---|
| O | S | O | S | S | Cl | Cl | Cl | Cl | cyclohexenyl | H | Et | n-Butyl |
| O | O | O | O | NH | H | phenyl-CH₃ | H | H | furyl | H | Me | n-Pr |
| O | O | O | O | S | H | Cl | H | CF₃ | —C≡CH | H | Et | n-Pr |
| S | S | O | O | NH | H | N(CH₃)₂ | H | H | methylthienyl | H | Et | Et |
| S | O | O | O | S | H | NO₂ | Cl | H | H | CN | Et | n-Pr |
| O | S | S | O | S | H | CN | H | H | methylpyridyl | H | Et | n-Pr |
| S | O | O | O | S | H | S(=O)₂SCH₃ | H | H | —CH=CHCH₃ | H | Et | n-Pr |
| O | O | S | O | S | H | OCH₃ | H | H | —C(=O)OCH₃ | H | Et | n-Pr |
| S | O | O | O | S | H | CH₂S(=O)₂CH₃ | H | H | —C(=O)CH₃ | H | Et | i-Pr |
| O | O | O | O | S | H | Br | H | H | H | CH₃ | Me | i-Butyl |
| S | S | O | O | S | H | —SO₂CH₂Cl | H | H | —C(=O)NHCH₃ | H | Et | n-Pr |
| O | O | S | O | NH | H | | H | H | | H | Et | i-Pr |

-continued
| A | B | Z | X | Y | R1 | R2 | R3 | R4 | R5 | R6 | R7 | R8 |
|---|---|---|---|---|----|----|----|----|----|----|----|----|
| O | O | O | O | NH | H | CN | H | H |  | H | Me | n-Pr |
| A | B | Z | X | Y | $R_1$ | $R_2$ | $R_3$ | $R_4$ | $R_5$ | $R_6$ | $R_7$ | $R_8$ |
|---|---|---|---|---|----|----|----|----|----|----|----|----|
| S | S | O | O | S | H | $CF_3$ | Cl | H | $CH_3$ | H | Et | n-Pr |
| O | O | S | O | S | H | H | H | H |  | H | Et | n-Pr |
| S | O | O | O | NH | H | $SCH_3$ | H | H |  | H | Et | i-Pr |
| O | O | S | O | S | H | $-CH_2N(CH_3)_2$ | OEt | H | $-CH_2SCH_3$ | H | Et | n-Butyl |
| O | O | S | O | NH | H | H | H | H | $-(CH_2)_5-$ | H | Et | i-Pr |
| S | O | O | S | NH | $OCH_3$ | H | H | H | $-(CH_2)_3N(CH_3)_2$ | H | n-Pr | i-Pr |
| O | O | O | O | S | H | Cl | H | Cl |  | H | Et | n-Pr |
Et = ethyl
Pr = propyl Selected species of the new compounds were evaluated to determine their pesticidal activity against mites, mite eggs, an aphia, a caterpillar, a beetle, and a fly.

Suspensions of the test compounds were prepared by dissolving one gram of compound in 50 ml of acetone in which had been dissolved 0.1 g (10 percent of the weight of the compound) of an alkylphenoxy polyethoxyethanol surfactant, as an emulsifying or dispersing agent. The resulting solution was mixed into 150 ml of water to give roughly 200 ml of a suspension containing the compound in finely divided form. The thus-prepared stock suspension contained 0.5 percent by weight of compound. The concentrations in parts per million by weight employed in the tests described hereinbelow were obtained by appropriate dilutions of the stock suspension with water. The test procedures were as follows;

Bean Aphid Foliage Spray Test

Adults and nymphal stages of the bean aphid (*Aphis fabae* Scop.) reared on potted dwarf nasturtium plants at 68°–70° F. and 50±5 percent relative humidity, constituted the test insects. For testing purposes, the number of aphids per pot was standardized to 100–150 by trimming plants containing excess aphids.

The test compounds were formulated by diluting the stock suspension with water to give a suspension contining 500 parts of test compound per million parts of final formulation.

The potted plants (one pot per compound tested) infested with 100–150 aphids were placed on a revolving turntable and sprayed with 100–110 milliliters of test compound formulation by use of a DeVilbiss spray gun set at 40 psig air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previousy ruled to facilitate counting. Temperature and humidity in the test room during the 24 hour holding period were 69°–70° F. and 50±5 percent, respectively. Aphids which fell onto the paper and were unable to remain standing after being uprighted were considered dead. Aphids remaining on the plant were observed closely for movement and those which were unable to move the length of the body upon stimulation by prodding were considered dead. Percent mortality was recorded for various concentration levels.

Southern Armyworm Leaf Spray Bait Test

Larvae of the southern armyworm (*Spodoptera eridania* (Cram.)), reared on Tendergreen bean plants at a temperature of 80°+5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulations by use of a DeVilbiss spray gun set at 40 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larve of the Mexican bean beetle (*Epilachna varivestis*, Muls.), reared on Tendergreen bean plants at a temperature of 80±5° F. and 50±5 percent relative humidity, were the test insects.

The test compounds were formulated by diluting the stock suspension with water to give a suspension containing 500 parts of test compound per million parts of final formulation. Tendergreen bean plants of standard height and age were placed on a revolving turntable and sprayed with 100–110 milliliters of test compound formulation by use of a DeVilbiss spray gun set at 40 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistener filter paper. Five randomly selected larvae were introduced into each dish, and the dishes were closed. The closed dishes were labeled and held at a temperature of 80+5 F., for three days. Although the larvae could easily consume the leaf within 24 to 48 hours, no more food was added. Larvae which were unable to move the length of the body even upon stimulation, were considered dead.

Southern Armyworm Ovicide Test

The test organism was the egg of the Southern armyworm (*Spodoptera eridania* (Cram.)) as obtained from adults reared on Tendergreen bean plants at a temperature of 80°±5° F. and a relative humidity of 50±5 percent. The eggs were laid on freezer paper (Marlon 717, Copco paper). The paper was then cut into small sections containing one or two egg masses.

The test compounds were formulated by diluting the stock suspension with water to give a suspension containing 500 parts of test compound per million parts of final formulation. The egg masses were dipped until they were thoroughly wet (5–10 seconds). They were then placed on a paper towel face up and were allowed to dry for 15–30 minutes. The dry eggs were placed in a 15×60 mm petri dish containing a cotton dental wick saturated with a 5 percent sodium chloride solution to maintain a high level of humidity. The closed dishes were labeled and held at a temperature of 80°±5° F. for four days. Larvae that emerged from the eggs, even if dead at the time of observation, were recorded as hatched.

Mite Foliage spray Test

Adults and nymphal stage of the two-spotted mite (*Tetranychus urticae* Koch), reared on Tendergreen bean plans at 80±5 percent relative humidity, were the test organisms. Infested leaves from a stock culture were placed on the primary leaves of two bean plants six to eight inches in height, growing in a two-and-a-half inch clay pot. 150–200 mites, a sufficient number for testing, were transferred from the excised leaves to the fresh plants in a period of twenty-four hours. Following the twenty-four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100–110 milliliters of test compound formulation by use of a DeVilbiss spray gun set at 40 psig. air pressure. This application which last 25 seconds, was sufficient to wet the plants to run-off. As a control, 100–110 milliliters of a water solution containing acetone and emulsifier in the same concentrations as the test compound formulations, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considered living.

Fly Bait Test

Four to six day old adult house flies (*Musca domestica*, L.) reared according to the specifications of the Chemical Specialties Manufacturing Association (Blue Book, McNair-Dorland Co., N.Y. 1954; pages 243–244, 261) under controlled conditions of 80°±5° F. and 50±5 percent relative humidity, were the test insects. The flies were immobilized by anesthetizing with carbon dioxide and twenty-five immobilized individuals, males and females, were transferred to a cage consisting of a standard food strainer about five inches in diameter which was inverted over a wrapping-paper-covered surface. Thes test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of an absorbent cotton pad. This bait cup was introduced and centered on the blotting paper under the food strainer prior to admitting the anesthetized flies. The caged flies were allowed to feed on the bait for twenty-four hours, at a temperature of 80±5° F. and a relative humidity of 50±5 per cent. Flies which showed no sign of movement on prodding were considered dead.

The results of these tests together with physical properties of the tested compounds are set forth in Table 1 below. In these tests the pesticidal activity of the compounds at the indicated dosage rate against aphid, mite, Southern Armyworm, Bean Beetle, and housefly was rated as follows:

A=excellent control (complete kill) at 500 ppm
B =partial control (moderate kill) at 500 ppm
C =no control (little or no kill) at 500 ppm The compounds contemplated in this invention may be applied as insecticides and miticides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Non-ionic, anionic, amphoteric, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable power, dust or granulated compositions, the active ingredient is dispersed in and on an apropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be aplied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein control the population of insects, mites and of ova mites and insects upon plants or other material to which the pesticides are applied. Generally, when used in sufficient amount to kill or repel the insects, they do not burn or injure the plant. The toxicants are compatible with substantially any other constituents of the spray schedule, and they may be used in the soil, upon the seeds, or the roots of plants without injuring either the seeds or roots of plants. They may also be used in combination with other pesticidally active compounds.

TABLE I
BIOLOGICAL AND ANALYTICAL PROPERTIES OF THE COMPOUNDS OF THIS INVENTION

| STRUCTURE | ANALYTICAL | Bean Aphid | Two Spotted Mite | Southern Armyworm | Bean Beetle | House Fly |
|---|---|---|---|---|---|---|
| [structure 1]<br>O—[1-(2-benzothiazolyl)-methyl]<br>O—ethyl-S—n-propyl thiophosphate | $C_{13}H_{18}NO_3PS_2$<br>Calc: C, 47.11; H, 5.47; N, 4.23<br>Found: C, 45.87; H, 5.63; N, 4.46<br>Oil | A | A | A | A | A |
| [structure 2]<br>O—[1-(2-benzothiazolyl)-ethyl]<br>O—ethyl-S—n-propyl thiophosphate | $C_{14}H_{20}NO_3PS_2$<br>Calc: C, 48.68; H, 5.84; N, 4.06<br>Found: C, 49.08; H, 5.64; N, 4.21<br>oil | A | A | A | B | C |
| [structure 3]<br>S—[1-(2-benzoxazolyl)<br>O—ethyl-S—n-propyl aithiophosphate | $C_{14}H_{20}NO_3PS_2$<br>Calc: C, 48.68; H, 5.84; N, 4.06<br>Found: C, 47.56; H, 5.98; N, 4.26<br>oil | A | A | A | A | A |

TABLE II

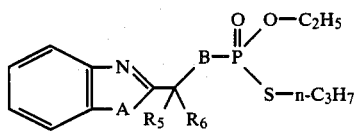

| | | LD$_{50}$ (ppm) | | | | |
|---|---|---|---|---|---|---|
| X | Y | BEAN APHID | TWO SPOTTED MITE | SOUTHERN ARMYWORM | BEAN BEETLE | HOUSE FLY |
| S | O | 60 | 35 | 70 | 500 | inactive |
| O | S | 8 | 1 | 31 | 80 | 16 |

LD$_{50}$ (ppm) is the concentration in parts per million that will give 50% kill of a given population. The test procedures are identical to those previously described except that the concentration of toxicant is varied.

Since phosphates of the benzoxazole structures in general give activities comparable to similar compounds with the benzothiazole moiety, Table II illustrates the enhanced activity of the phosphates of this invention when Y equals S.

I claim:

1. A compound having the formula selected from

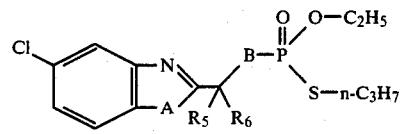

and

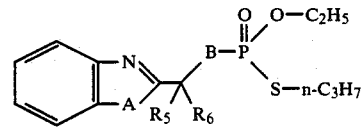

wherein:
A is O or S;
R$_5$ is hydrogen;
R$_6$ is alkyl; and
B is O or S.

2. The compound of claim 1 having the formula

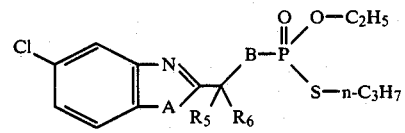

wherein:
A is O or S;
R$_5$ is hydrogen;
R$_6$ is alkyl; and
B is S.

3. The compound of claim 1 having the formula

[structure]

wherein:
A is O;

R₅ is hydrogen;
R₆ is alkyl; and
B is O.

4. The compound of claim 1 having the formula selected from

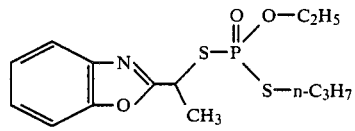

S-[1-(2-benzoxazolyl)-ethyl]-0-ethyl-S-n-propyl dithiophosphate,

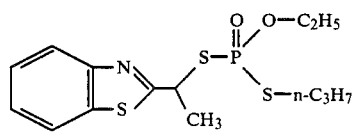

S-[1-(2-benzothiazolyl)-ethyl]-0-ethyl-S-n-propyl dithiophosphate, and

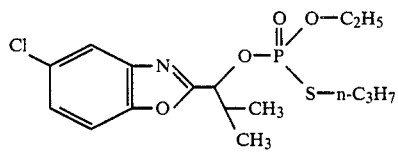

0-(1-[2-(5-chlorobenzoxazolyl)]-2-methylpropyl)-0-ethyl-S-n-propyl thiophosphate.

5. The compound of claim 1 having the formula

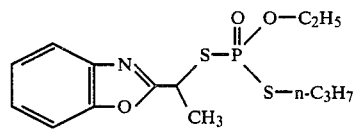

S-[1-(2-benzoxazolyl)-ethyl]-0-ethyl-S-n-propyl dithiophosphate.

6. The compound of claim 1 have the formula

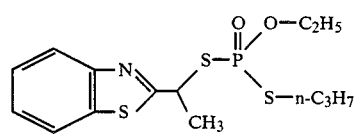

S-[1-(2-benzothiazolyl)-ethyl]-0-ethyl-S-n-propyl dithiophosphate.

7. The compound of claim 1 having the formula

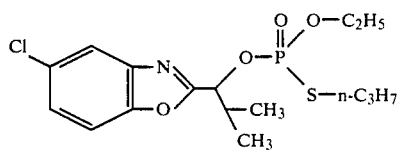

0-(1-[2-(5-chlorobenzoxazolyl)]-2-methylpropyl)-0-ethyl-S-n-propyl thiophosphate.

8. An insecticidal and miticidal composition comprising an acceptable carrier and as the active toxicant, an insecticidally or miticidally effective amount of the compound of claim 1.

9. An insecticidal and miticidal composition comprising an acceptable carrier and as the active toxicant, an insecticidally or miticidally effective amount of the compound of claim 2.

10. An insecticidal and miticidal composition comprising an acceptable carrier and as the active toxicant, an insecticidally or miticidally effective amount of the compound of claim 3.

11. An insecticidal and miticidal composition comprising an acceptable carrier and as the active toxicant, an insecticidally or miticidally effective amount of the compound of claim 4.

12. An insecticidal and miticidal composition comprising an acceptable carrier and as the active toxicant, an insecticidally or miticidally effective amount of the compound of claim 5.

13. An insecticidal and miticidal composition comprising an acceptable carrrier and as the active toxicant, an insecticidally or miticidally effective amount of the compound of claim 6.

14. An insecticidal and miticidal composition comprising an acceptable carrier and as the active toxicant, an insecticidally or miticidally effective amount of the compound of claim 7.

15. A method of controlling insects and mites which comprises subjecting them to an insecticidally or miticidally effective amount of the compound of claim 1.

16. A method of controlling insects and mites which comprises subjecting them to an insecticidally or miticidally effective amount of the compound of claim 2.

17. A method of controlling insects and mites which comprises subjecting them to an insecticidally or miticidally effective amount of the compound of claim 3.

18. A method of controlling insects and mites which comprises subjecting them to an insecticidally or miticidally effective amount of the compound of claim 4.

19. A method of controlling insects and mites which comprises subjecting them to an insecticidally or miticidally effective amount of the compound of claim 5.

20. A method of controlling insects and mites which comprises subjecting them to an insecticidally or miticidally effective amount of the compound of claim 6.

21. A method of controlling insects and mites which comprises subjecting them to an insecticidally or miticidally effective amount of the compound of claim 7.

* * * * *